US005703273A

United States Patent [19]

Stern et al.

[11] Patent Number: 5,703,273
[45] Date of Patent: Dec. 30, 1997

[54] PROCESS FOR PREPARING N-PHOSPHONOMETHYLAMINO CARBOXYLIC ACIDS

[75] Inventors: Michael K. Stern, University City; Brian K. Cheng, Chesterfield; Jerry R. Ebner, St. Peters; Dennis P. Riley, Ballwin, all of Mo.

[73] Assignee: Monsanto Company, St. Louis, Mo.

[21] Appl. No.: 674,211

[22] Filed: Jul. 1, 1996

Related U.S. Application Data

[63] Continuation of Ser. No. 428,972, Apr. 26, 1995, abandoned, which is a continuation-in-part of Ser. No. 269,722, Jul. 1, 1994, abandoned.
[51] Int. Cl.$^6$ .................................................. C07F 9/38
[52] U.S. Cl. .................................................. 562/16; 562/17
[58] Field of Search ..................................... 562/16, 17

[56] References Cited

U.S. PATENT DOCUMENTS

| | | |
|---|---|---|
| 2,661,364 | 12/1953 | Ernsberger et al. . |
| 3,567,768 | 3/1971 | Shen et al. . |
| 4,062,491 | 12/1977 | Pfliegel et al. . |
| 4,439,373 | 3/1984 | Nagubandi . |
| 4,442,041 | 4/1984 | Subramanian . |
| 4,547,324 | 10/1985 | Wong et al. . |
| 4,810,426 | 3/1989 | Fields, Jr. et al. . |
| 4,847,013 | 7/1989 | Müller . |
| 4,965,403 | 10/1990 | Fields, Jr. et al. . |
| 5,041,628 | 8/1991 | Donadello . |
| 5,292,936 | 3/1994 | Franczyk . |

FOREIGN PATENT DOCUMENTS

| | | |
|---|---|---|
| 402 887 A1 | 6/1990 | European Pat. Off. . |

OTHER PUBLICATIONS

Ivanov et al., "Phosphomethylation of p–Substituted Anilines." *A. E. Arbuzov Institute of Organic and Physical Chemistry*, Kazan Branch of the Academy of Sciences of the USSR, Translated from Izvestiya Akademii Nauk SSSR, Seriya Khimicheskaya, No. 1, pp. 178–180 (Jan. 1982) (original article submitted Feb. 24, 1981).

Jaron, A.W. et al, "Preparation of N–phosphonomethylglycine and its derivatives as herbicides", *Chemical Abstracts*, vol. 220, No. 15, Apr. 10, 1989, Columbus, Ohio, U.S. Abstract No. 135712u.

Fields, "The Synthesis of Esters of Substituted Amino Phosphonic Acids", *J. Am. Chem. Soc.*, vol. 74, pp. 1528–1531 (1952).

Moedritzer and Irani, "The Direct Synthesis of α–Aminomethylphosphonic Acids. Mannich–Type Reactions with Orthophosphorous Acid", *J. Org. Chem.*, vol. 31, pp. 1603–1607 (1966).

Baruskov et al, "Synthesis of New Complexons and Their Derivatives", *Zhurnal Obshchei Khimii*, vol. 53, No. 6, pp. 1243–1249 (1983).

Baruskov et al "Synthesis of New Complexons of the Aliphatic Series and Investigation of the Mechanism of Acidic Dissociation", *Zhurnal Obshchei Khimii*, vol. 55, No. 7, pp. 1594–1600 (1985).

*Primary Examiner*—Samuel Barts
*Attorney, Agent, or Firm*—Monsanto Company Arnold, White & Durkee

[57] ABSTRACT

A process for preparing N-hydroxyalkylaminomethylphosphonic acid or salts thereof which comprises contacting an alkanolamine, formaldehyde and a trialkyl phosphite under suitable reaction conditions to produce a reaction mixture, and hydrolyzing the reaction mixture under neutral, acidic or basic conditions. In one embodiment, the N-hydroxyalkylaminomethylphosphonic acid or salts thereof is catalytically oxidized to produce an N-phosphonomethylaminocarboxylic acid or salts thereof.

41 Claims, No Drawings

PROCESS FOR PREPARING N-PHOSPHONOMETHYLAMINO CARBOXYLIC ACIDS

CROSS REFERENCE TO RELATED APPLICATION

This application is a continuation of application Ser. No. 08/428,972, filed Apr. 26, 1995, now abandoned, which is a continuation-in-part of application Ser. No. 08/269,722, filed Jul. 1, 1994 now abandoned.

BACKGROUND OF THE INVENTION

This invention relates to a process for preparing N-hydroxyalkylaminomethylphosphonic acid or salts thereof. In one aspect, this invention relates to a new and useful process for preparing N-hydroxyalkyl-aminomethylphosphonic acid or salts thereof from an alkanolamine, formaldehyde and a trialkyl phosphite. In another aspect, this invention relates to a process for preparing N-phosphonomethylaminocarboxylic acid or salts thereof by the catalytic oxidation of N-hydroxyalkylaminomethylphosphonic acid or salts thereof. In yet another aspect, this invention relates to a process for preparing N-phosphonomethylglycine useful as a herbicide.

N-Hydroxyalkylaminomethylphosphonic acid or salts thereof are useful as a raw material in the preparation of agricultural chemicals. N-Phosphonomethylaminocarboxylic acids or salts thereof are useful as agricultural chemicals. Specifically, N-phosphonomethylglycine, known also by its common name glyphosate, is a highly effective and commercially important phytotoxicant useful in controlling a large variety of weeds and crops. It is applied to the foliage of a very broad spectrum of perennial and annual grasses and broad-leafed plants to achieve the desired control. Industrial uses include control of weeds along roadsides, waterways, transmission lines, in storage areas, and in other nonagricultural areas. Usually glyphosate is formulated into herbicidal compositions in the form of its various salts which retain the anionic form of glyphosate in solution, preferably in water.

The reaction of a primary amine with an aldehyde and a phosphite diester is disclosed in Fields, "The Synthesis of Esters of Substituted Amino Phosphonic Acids", J. Am. Chem. Soc., Vol. 74, pp. 1528–31 (1952). However, the reaction product contains considerable amounts of the undesirable bis-phosphonomethylated product. Similarly, the reaction of a primary amine with formaldehyde and phosphorous acid is disclosed in Moedritzer and Irani, "The Direct Synthesis of α-Aminomethylphosphonic Acids. Mannich-Type Reactions with Orthophosphorous Acid", J. Org. Chem., Vol. 31, pp. 1603–1607 (1966). As in Fields, the reaction product is predominantly the bis-phosphonomethylated product.

Barsukov et al, "Synthesis of New Complexons and Their Derivatives", Zhurnal Obshchei Khimii, Vol. 53, No. 6, pp. 1243–49 (1983) and Barsukov et al, "Synthesis of New Complexons of the Aliphatic Series and Investigation of the Mechanism of Acidic Dissociation", Zhurnal Obshchei Khimii, Vol. 55, No. 7, pp. 1594–1600 (1985) disclose the reaction of ethanolamine with paraformaldehyde and dimethyl hydrogen phosphite with a mole ratio of amine/phosphite of 1.0 and a mole ratio of formaldehyde/phosphite of 1.0. While these articles disclose that the product is the mono-phosphonomethylated compound, reproduction of the reaction disclosed in the experimental section resulted in no mono-phosphonomethylated product being produced, i.e. $^{31}$P-NMR of the material produced in the reproduction of the Barsukov example showed a 0% yield of N-(2-hydroxyethyl)-aminomethylphosphonic acid (See Example 5 herein). The process as described in the Barsukov et al articles is, therefore, incapable of preparing N-hydroxyalkylaminomethylphosphonic acid in a commercially practicable manner.

A process for preparing N-hydroxyalkylaminomethylphosphonic acid or salts thereof which is economical, commercially viable, and can produce essentially only the mono-phosphonomethylated product is highly desirable.

SUMMARY OF THE INVENTION

It is an object of the invention to provide an efficient and economical process for preparing N-hydroxyalkylaminomethylphosphonic acid or salts thereof that is commercially viable. It is a further object of the invention to provide a process for preparing N-hydroxyalkylaminomethylphosphonic acid or salts thereof for use in the production of N-phosphonomethylaminocarboxylic acid or salts thereof. It is a further object of the invention to provide an efficient and economical process for preparing N-phosphonomethylaminocarboxylic acid or salts thereof for use as agricultural chemicals. It is still a further object of the invention to provide an efficient and economical process for preparing N-phosphonomethylglycine that is commercially viable.

According to the invention, a process for preparing N-hydroxyalkylaminomethylphosphonic acid or salts thereof is provided which comprises contacting an alkanolamine, formaldehyde and a trialkyl phosphite under suitable reaction conditions to produce a reaction mixture, and hydrolyzing the reaction mixture under neutral, acidic or basic conditions. In one embodiment, the N-hydroxyalkylaminomethylphosphonic acid or salts thereof is catalytically oxidized to produce an N-phosphonomethylaminocarboxylic acid or salts thereof.

Further according to the invention, a process for preparing N-hydroxyalkylaminomethylphosphonic acid or salts thereof is provided which comprises contacting an alkanolamine, formaldehyde and a trialkyl phosphite in the presence of an alcohol under suitable reaction conditions to produce a reaction mixture, and hydrolyzing the reaction mixture under neutral, acidic or basic conditions. In one embodiment, the N-hydroxyalkylaminomethylphosphonic acid or salts thereof is catalytically oxidized to produce an N-phosphonomethylaminocarboxylic acid or salts thereof.

Still further according to the invention, a process for preparing N-phosphonomethylglycine or salts thereof is provided which comprises contacting ethanolamine, formaldehyde and a trialkyl phosphite under suitable reaction conditions to produce a reaction mixture, hydrolyzing the reaction mixture under neutral, acidic or basic conditions to produce N-hydroxyethylaminomethylphosphonic acid or salts thereof, and catalytically oxidizing the N-hydroxyethylaminomethylphosphonic acid or salts thereof.

DETAILED DESCRIPTION OF THE INVENTION

The invention relates to a process for preparing N-hydroxyalkylaminomethylphosphonic acid represented by the formula

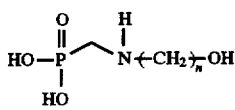

or salts thereof comprising (a) contacting an alkanolamine represented by the formula

wherein n is 2 to 6, formaldehyde and a trialkyl phosphite under suitable conditions of time and temperature to produce a reaction mixture wherein the molar ratio of alkanolamine to phosphite is about 1:1 to about 15:1, and (b) hydrolyzing the reaction mixture under neutral, acidic or basic conditions.

The invention further relates to a process for preparing N-hydroxyalkylaminomethylphosphonic acid represented by the formula

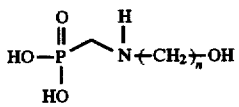

or salts thereof comprising (a) contacting an alkanolamine represented by the formula $H_2N-(CH_2)_n-OH$ wherein n is 2 to 6, formaldehyde and a trialkyl phosphite in the presence of an alcohol represented by the formula $R(OH)_m$, wherein R is an alkyl group having 1 to about 18 carbon atoms and m is 1 to 3, under suitable conditions of time and temperature to produce a reaction mixture wherein the molar ratio of alkanolamine to phosphite is 1:1 to about 5:1, and (b) hydrolyzing the reaction mixture under neutral, acidic or basic conditions.

For producing N-phosphonomethylaminocarboxylic acid or represented by the formula

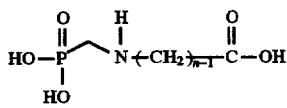

or salts thereof, the processes of the invention further comprise (c) catalytically oxidizing the N-hydroxyalkylaminomethylphosphonic acid or salts thereof.

The invention still further relates to a process for preparing N-phosphonomethylglycine or salts thereof comprising (a) contacting ethanolamine, formaldehyde and a trialkyl phosphite under suitable reaction conditions of time and temperature to produce a reaction mixture wherein the molar ratio of ethanolamine to phosphite is about 1:1 to about 15:1, (b) hydrolyzing the reaction mixture under neutral, acidic or basic conditions to produce N-hydroxyethylaminomethylphosphonic acid or salts thereof, and (c) catalytically oxidizing the N-(2-hydroxyethyl)aminomethylphosphonic acid or salts thereof.

As used herein, the term "salts of N-hydroxyalkylaminomethylphosphonic acid" means alkali metal or alkaline earth metal salts of N-hydroxyalkylaminomethylphosphonic acid and the term "salts of N-phosphonomethylaminocarboxylic acid" means alkali metal or alkaline earth metal salts of N-phosphonomethylaminocarboxylic acid. Thus, the products of the hydrolysis and oxidation reactions can include the acid, the salts thereof or any combination thereof, depending on the specific reaction and reaction conditions selected.

Alkanolamines that can be employed according to the invention are represented by the formula

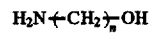

wherein n is 2 to 6. Examples of alkanolamines include ethanolamine, 3-amino-1-propanol, 4-amino-1-butanol, 5-amino-1-pentanol, 6-amino-1-hexanol and mixtures thereof. The currently preferred alkanolamine is ethanolamine because of ready availability and the commercial significance of the product prepared using ethanolamine as the starting material.

Formaldehyde can be employed according to the invention as paraformaldehyde or as an aqueous solution of formaldehyde. Aqueous formaldehyde is commercially available as 37–50 weight percent aqueous solutions which may contain methanol, ethanol, or n-butanol.

Trialkyl phosphites, useful in the process of the invention, are commercially available or are readily prepared by conventional methods such as by reacting $PCl_3$ with an alcohol including polyols. If a polyol is used as a reactant, the phosphite product could have a cyclic structure, i.e. a cyclic phosphite ester. See, for example, Ford-Moore et al., Org. Syn., Coll. Vol. IV, p. 955 and Cook et al., J. Chem. Soc., 635 (1949) for methods utilizing $PCl_3$. Trialkyl phosphites can be represented by the formula $P(OR')_3$ wherein R' is an alkyl group. The alkyl groups of the trialkyl phosphites are linear or branched alkyl groups having 1 to 18 carbon atoms and are optionally substituted with —OH groups. The preferred alkyl groups are those that are branched or sterically hindered, or substituted with an —OH group. The most preferred alkyl groups are those having 2 to 6, especially 3 to 4, carbon atoms. The preferred trialkyl phosphite is triisopropyl phosphite. Trialkyl phosphites are preferred over dialkyl phosphites because of unexpectedly improved yields achievable with the trialkyl phosphites.

Examples of suitable trialkyl phosphites include, but are not limited to, tributyl phosphite, triisopropyl phosphite, trimethyl phosphite, triethyl phosphite, tridecyl phosphite, triisodecyl phosphite, triisooctyl phosphite, trilauryl phosphite, 1-methyl-4-phospha-3,5,8-trioxabicyclo[2,2,2]octane, 5-phospha-4,6,9-trioxabicyclo[3,3,1]nonane and mixtures thereof. The amount of alkanolamine utilized in the process of the invention can be expressed as a molar ratio of alkanolamine starting material to phosphite starting material. Broadly, the molar ratio of alkanolamine to phosphite is about 1:1 to about 15:1. When the number of carbon atoms in the alkyl group of the trialkylphosphite is 2 to 6, the molar ratio of alkanolamine to phosphite is preferably about 1.2:1 to about 8:1, and most preferably about 1.5:1 to about 2.5:1. When the number of carbon atoms in the alkyl group of the trialkylphosphite is 1 or greater than 6, the molar ratio of alkanolamine to phosphite is preferably about 1:1 to about 10:1, and most preferably about 1.5:1 to about 8:1. The excess alkanolamine present in the process of the invention also serves as the reaction solvent.

The amount of formaldehyde utilized in the process of the invention can be expressed as a molar ratio of formaldehyde starting material to phosphite starting material. Broadly, the molar ratio of formaldehyde to phosphite is 1:1 to about 5:1, preferably 1:1 to about 2:1, and most preferably 1:1 to about 1.5:1.

The reaction of alkanolamine, formaldehyde and phosphite is conducted at a suitable temperature which can vary over a wide range. The reaction temperature will generally be within the range of about 50° C. to about 150° C., preferably about 60° C. to about 120° C. and most preferably about 70° C. to about 110° C. The reaction of alkanolamine, formaldehyde and phosphite is conducted for a suitable time which can vary over a wide range depending on various parameters, e.g. the reaction temperature. Generally, the reaction time will be within the range of the time necessary for the phosphite to be consumed to about 16 hours, preferably about 2 hours to about 16 hours, and most preferably about 4 hours to about 6 hours.

The reaction of alkanolamine, formaldehyde and phosphite can optionally be conducted in the presence of an alcohol solvent wherein the alcohol is represented by the formula $R(OH)_m$ and R is an alkyl group having 1 to about 18 carbon atoms and m is 1 to 3. The alkyl group, R, can be linear or branched and preferably is the same alkyl group as that utilized in the trialkyl phosphite starting material.

Examples of suitable alcohols include, but are not limited to, methanol, ethanol, isopropanol, n-butanol, 2-butanol, isooctanol, decyl alcohol, isodecyl alcohol, lauryl alcohol, ethylene glycol, 1,2-propylene glycol, 1,3-propylene glycol, glycerol, 2-hydroxymethyl-2-methyl-1,3-propanediol, 1,3,5-trihydroxycyclohexane and mixtures thereof.

When the reaction of alkanolamine, formaldehyde and phosphite is conducted in the presence of an alcohol solvent, the molar ratio of alkanolamine starting material to phosphite starting material is 1:1 to about 5:1, preferably 1.2:1 to about 3:1, and most preferably about 1.5:1 to about 2:1.

The hydrolysis reaction can be conducted under neutral, acidic or basic conditions using any one of several conventional methods known to those skilled in the art. When the hydrolysis reaction is conducted under acidic conditions, a preferred method is to remove the excess alkanolamine from the reaction mixture together with any alcohol co-solvent optionally present followed by hydrolyzing the reaction mixture in hydrochloric acid. The concentration of the hydrochloric acid is preferably in the range of 6 N HCl to 12 N HCl (concentrated HCl). The temperature for the acid hydrolysis reaction is generally in the range of the boiling point of the HCl to about 250° C., preferably 80° C. to 120° C. Generally, the reaction time will be within the range of the time necessary for hydrolysis to occur to about 24 hours, preferably about 2 hours to about 16 hours. After the hydrolysis reaction is completed, the N-hydroxyalkylaminomethylphosphonic acid can be recovered by any conventional method known to those skilled in the art, such as the method utilized in Example 1.

When the hydrolysis reaction is conducted under basic conditions, a preferred method is to contact the reaction mixture with an alkali metal hydroxide or alkaline earth metal hydroxide, preferably an alkali metal hydroxide. The concentration of the alkali metal hydroxide or alkaline earth metal hydroxide is broadly within the range of about 15 weight percent to about 90 weight percent, preferably about 40 weight percent to about 60 weight percent, and most preferably about 50 weight percent. The amount of alkali metal hydroxide or alkaline earth metal hydroxide utilized in the hydrolysis reaction can be expressed as the ratio of equivalents of hydroxide to moles of phosphite starting material. Broadly, the ratio is about 2:1 to about 5:1, preferably about 2.5:1 to about 4:1, and most preferably about 3:1.

In the preferred embodiment of the hydrolysis conducted under basic conditions, the alcohol formed during the hydrolysis, i.e. the alcohol corresponding to the alkyl groups in the trialkyl phosphite, is removed from the reaction mixture during hydrolysis, such as by distillation. For example, when triisopropyl phosphite is utilized in the process isopropyl alcohol is removed during the hydrolysis. Conducting the hydrolysis under these conditions compared to conducting the hydrolysis without removing the alcohol formed results in unexpectedly increased yield of N-hydroxyalkylaminomethylphosphonic acid.

The alkali metal hydroxides for use in the process of the invention include lithium hydroxide, sodium hydroxide, potassium hydroxide, rubidium hydroxide and cesium hydroxide. Because of their ready availability and ease of handling, sodium hydroxide and potassium hydroxide are preferred, and sodium hydroxide is especially preferred.

The alkaline earth metal hydroxides for use in the process of the invention include beryllium hydroxide, magnesium hydroxide, calcium hydroxide, strontium hydroxide and barium hydroxide. Calcium hydroxide is currently preferred because of its ready availability.

The temperature for the base hydrolysis reaction is generally in the range of about 80° C. to about 250° C., preferably about 80° C. to about 180° C., most preferably about 120° C. to about 150° C. Generally, the reaction time will be within the range of the time necessary for hydrolysis to occur to about 48 hours, preferably 2 hours to about 24 hours and most preferably about 2 hours to about 16 hours. After the hydrolysis reaction is completed, the N-hydroxyalkylaminomethylphosphonic acid or salts thereof can be recovered by any conventional method known to those skilled in the art such as the method utilized in Example 1.

When the hydrolysis reaction is conducted under neutral conditions, a preferred method is to contact the reaction mixture with water. The concentration of the reactant to be hydrolyzed, i.e. the intermediate esters of N-hydroxyalkylaminomethylphosphonic acid, in water is broadly within the range of about 40 weight percent to about 5 weight percent, preferably about 30 weight percent to about 15 weight percent. The temperature for the neutral hydrolysis reaction is generally in the range of about 120° C. to about 320° C., preferably about 180° C. to about 260° C. Generally, the reaction time will be within the range of the time necessary for hydrolysis to occur to about 24 hours, preferably about 5 hours to about 15 hours. After the hydrolysis reaction is completed, the N-hydroxyalkylaminomethylphosphonic acid or salts thereof can be recovered by any conventional method known to those skilled in the art.

The oxidation of the N-hydroxyalkylaminomethylphosphonic acid or salts thereof is conducted in the presence of a catalyst. Suitable oxidation catalysts are well known to those skilled in the art such as Raney copper and those described in U.S. Pat. No. 4,810,426 and U.S. Pat. No. 5,292,936, which are both incorporated by reference herein.

In U.S. Pat. No. 4,810,426, the oxidation of N-(2-hydroxyethyl)aminomethylphosphonic acid is conducted with an alkali metal hydroxide in the presence of water and a suitable catalyst select from cadmium, zinc, copper, palladium and platinum and their respective oxides, hydroxides and salts. The oxidation reaction is conducted at a temperature of 200° C. to 300° C.

In U.S. Pat. No. 5,292,936, the oxidation of N-(2-hydroxyethyl)aminomethylphosphonic acid is conducted with an alkali metal hydroxide in the presence of an effective amount of a Raney copper catalyst containing from about 50 parts per million to about 10,000 parts per million of an element selected from the group consisting of chromium, titanium, niobium, tantalum, zirconium, vanadium, molybdenum, manganese, tungsten, cobalt, nickel and mixtures thereof. Of the above elements, chromium, molybdenum, and mixtures of chromium and molybdenum are preferred. The oxidation reaction is conducted at a temperature between about 120° C. and 220° C.

Another particularly applicable type of oxidation catalysts are the supported mixed metal catalysts such as those described in U.S. patent application Ser. No. 08/269,722, and its subsequent continuation-in-part U.S. patent application Ser. No. 08/407,723, which are incorporated by reference herein. The supported mixed metal catalyst of the present invention is prepared by depositing from about 1 wt. % to about 50 wt. %, based on the total weight of the catalyst, of an element selected from the group consisting of copper, cobalt, nickel, cadmium and mixtures thereof on a hydroxide resistant support having from about 0.05 wt. % to about 10 wt. % of an anchor metal selected from the group consisting of platinum, palladium, ruthenium, silver, gold and mixtures thereof.

Suitable hydroxide resistant supports include titanium oxide, zirconium oxide and carbon. Carbon is preferred. Activated carbon is even more preferred.

The particulate anchor metal deposited on the hydroxide resistant support can be a noble metal. By noble metal is meant gold, silver, platinum, palladium, ruthenium or mixtures thereof. Platinum or palladium are preferred. Platinum is most preferred. The amount of anchor metal to be deposited on the hydroxide resistant support can vary from about 0.05 wt. % to about 10 wt. %, based on the total weight of the catalyst. When less than about 0.05 wt. % anchor metal is deposited on the hydroxide resistant support, there is insufficient anchor metal to combine with the copper, cobalt, nickel, and/or cadmium to provide a satisfactory catalyst. On the other hand, when more than about 10 wt. % anchor metal, based on the total weight of the catalyst, is deposited on the support, the crystallite size of plated metal tends to increase. Larger crystal sizes of the plated elemental metal sometimes leads to reduced catalytic performance. It is preferred to use from about 0.1 wt. % and about 5 wt. %, based on the total weight of the catalyst, of the anchor metal. The currently preferred supported mixed metal catalyst is a carbon supported mixture of copper and platinum or palladium.

Suitable hydroxide resistant supports containing a suitable anchor metal can be obtained commercially.

The amount of deposited metal (i.e., copper, cobalt, nickel and/or cadmium) should be sufficient to cover at least some of the embedded anchor metal particles. In addition to the coated particles the presence of at least some particles of the plating metal embedded on the support but not adherent on the anchor metal can exist. X-ray Photoelectron Spectroscopy (XPS) is a technique which can be used to measure the relative concentration of surface atoms in the catalyst. Using this technique, it has been found that preferably in the catalysts of this invention the surface atomic ratio of the deposited metal to the anchor metal is greater than 2.0, and more preferably, the XPS surface atomic ratio is greater than the corresponding bulk atomic ratio.

Any number of techniques can be used to deposit the anchor metal on the alkali resistant substrate and to deposit the copper, cobalt, nickel, and/or cadmium onto the anchor metal. It is preferred, however, to use electroless metal deposition. Electroless metal deposition refers to the chemical deposition of an adherent metal coating on a suitable substrate in the absence of an externally applied electric source.

Regardless by the method of depositing the anchor metal onto the substrate, the size of the metal particles is a critical parameter in that it dictates the size of the crystals of copper, cobalt, nickel and cadmium to be deposited. The crystallite size of the copper, cobalt, nickel, and cadmium should be less than about 500 Angstroms, and in the case of copper, it is preferred that the crystallite size is less than about 300 Angstroms. Although applicants do not wish to be bound by any particular theory, it is believed that a uniform distribution of the anchor metal is best for achieving high reaction yields, but not necessary fast reaction rates. Further, it is believed that it is important to have small, well-reduced, highly-dispersed anchor metal particles.

In practice, the substrate containing the anchor metal is added to and slurried in water. Next, a plating solution, e.g., copper plating solution, is prepared by mixing the plating solution in the appropriate proportions while the slurry of substrate and water is gently stirred at a temperature of about 0° C. up to 30° C. or higher in an open container. The plating solution containing a complexing agent and a reducing agent is added to the slurry in small increments by monitoring the pH with each addition. After an appropriate time interval, the next increment of the slurry is slowly added. The amount of plating solution added depends on the desired weight percent catalytic metal on the anchor metal in the catalyst. When the deposition of catalytic metal is completed, an essentially colorless filtrate results.

Next, the finished catalyst is filtered and washed with distilled water. The filtration must be done in an inert atmosphere, such as a nitrogen atmosphere, to avoid exposure of the catalyst to air. Washing the catalyst removes unreacted components such as parts per million impurities and unreacted reducing agent, such as formaldehyde. It has been found that from about 0.5 to 1.5 wt. % alkali metal is left on the catalyst, which is usually not harmful. The catalyst should be stored in a manner which avoids exposure to oxygen, preferably by being kept under water.

The currently preferred oxidation catalysts for use in the process of the invention are the catalysts of U.S. Pat. No. 5,292,936 and the supported mixed metal catalysts, with the supported mixed metal catalysts being especially preferred.

The reactions of the present invention can be conducted under atmospheric pressure or in a closed reaction vessel under a pressure. When the reactions are conducted in a pressure vessel, the pressure will generally be the vapor pressure of the reaction mixture at the reaction conditions.

EXAMPLES

General Procedures: Trialkyl and dialkyl phosphites were purchased from Aldrich Chemical when available. Phosphites which were not commercially available were synthesized from $PCl_3$ and the corresponding alcohol by the method of Ford-Moore et. al Org. Syn. Coll. Vol. IV p. 955 or the method of Cook et. al. J. Chem. Soc. 635, (1949). Formaldehyde was purchased from Aldrich Chemical as a 37% solution in water. Paraformaldehyde (91–93%) was obtained from Hoechst Celanese Corporation. The yield of N-hydroxyalkylaminomethylphosphonic acids or their salts were determined by $^{31}$P-NMR in $D_2O$ using methylenediphosphonic acid as an internal standard. Typically NMR samples were prepared in $D_2O$ containing conc. HCl such that a sample pH=0.7 was obtained. NMR spectra were obtained on Varian VXR-300 or Varian VXR-400 spectrometers. Qualitative and quantitative mass spectra were run on a Finnigan MAT90, a Finnigan 4500 and a VG40-250T spectrometers.

Example 1

This example illustrates the synthesis of sodium N-(2-hydroxyethyl)aminomethylphosphonate using triethylphosphite.

Triethylphosphite (16.6 g, 0.1 mmol), paraformaldehyde (3.0 g, 0.1 mmol) and ethanolamine (48.8 g, 0.8 mmol) was charged into a round bottom flask equipped with magnetic stir bar and reflux condenser. The reaction was heated to 100° C. for 16 h. Base hydrolysis of the intermediate esters was achieved by adding 2 equiv of NaOH (16 g of a 50% solution) and heating to 120° C. for 16 hours. The reaction was allowed to cool and was concentrated under vacuum. Methanol (100 mL) was added on the solvent was again removed under vacuum. This was repeated several times until a white solid formed the flask. The solid, which is a mixture of inorganic salts and sodium N-(2-hydroxyethyl) aminomethylphosphonate, was filtered and dried under vacuum to give 56% yield of sodium N-hydroxyethylaminomethylphosphonate. $^{31}$P-NMR obtained in $D_2O$ containing conc. HCl (pH=of sample is 0.7)δ=10.8 ppm. FAB-MS obtained in a glutathione/HCl matrix M+H=156.

It is also possible to hydrolyze the intermediate esters under acidic conditions. When this method is employed excess ethanolamine is first removed under vacuum to give a yellow oil. Concentrated HCl was added (50 mL) and the reaction was heated to reflux for 16 h. The solution was allowed to cool and was concentrated under vacuum. Sodium hydroxide (2 equiv. added as 10% solution) was added and the water was removed under vacuum to give an amber oil. Methanol (100 mL) was added and was immediately removed by evaporation. This was repeated three times which resulted in the precipitation of a white solid. The solid, which was a mixture of inorganic salts and sodium N-(2-hydroxyethyl)aminomethylphosphonate was collected by filtration, washed with ether and dried under vacuum to give 36% of sodium N-(2-hydroxyethyl) aminomethylphosphonate.

Summarized in Table 1 are the results of the reaction of various mole ratios triethylphosphite formaldehyde and ethanolamine under a variety of reaction conditions. All of the reaction contained in Table 1 followed the experimental procedures outline above. The yields of N-(2-hydroxyethyl) aminomethylphosphonic acid were determined by $^{31}$P-NMR.

TABLE 1

Preparation of N-2(-Hydroxyethyl)aminomethylphosphonic Acid Using Triethylphosphite

| Phosphite | Mole Ethanolamine | Formaldehyde | Reaction Temp °C. | Hydrolysis Method | % Yield[b] |
|---|---|---|---|---|---|
| 0.1 | 0.8 | 0.1 | 110 | acid | 83 |
| 0.1 | 0.8 | 0.2 | 70 | acid | 86 |
| 0.12 | 0.5 | 0.1 | 70 | acid | 66 |
| 0.12 | 0.8 | 0.1 | 100 | base | 61 |
| 0.12 | 0.8 | 0.12(p) | 70 | base | 66 |
| 0.2 | 0.5 | 0.1(p) | 100 | acid | 40 |
| 0.1 | 0.5 | 0.2(p) | 70 | acid | 58 |

[a]Formaldehyde was charged as a 37% solution in water. (p) denotes when paraformaldehyde was used.
[b]Yields determined by $^{31}$P-NMR and are based on moles of phosphite charged.

Example 2

This example illustrates the use of triisopropylphosphite in the synthesis of N-(2-hydroxyethyl) aminomethylphosphonic acid. Triisopropylphosphite (20.8 g, 0.1 mmol), paraformaldehyde (3.6 g, 0.12 mmol) and ethanolamine (48.8 g, 0.8 mmol) was charged into a round bottom flask equipped with magnetic stir bar and reflux condenser. The reaction was heated to 100° C. for 16 h. Base hydrolysis of the intermediate esters was achieved by adding 2 equiv. of NaOH (16 g of a 50% solution) and heating to 120° C. for 16 hours. The reaction was allowed to cool and was concentrated under vacuum. Water (30 mL) was added to the reaction mixture and a sample was removed for $^{31}$P-NMR analysis. Yield of N-(2-hydroxyethyl) aminomethylphosphonic acid (85%) was based on moles of phosphite charged.

Summarized in Table 2 are the results of reactions run with a similar experimental protocol as described above but with different trialkylphosphites and various ratios of reagents.

TABLE 2

Preparation of N-(2-Hydroxyethyl)aminomethylphosphonic Acid Using a Variety of Trialkylphosphites

| Phosphite | Mole Ethanolamine | Formaldehyde | Reaction Temp °C. | Hydrolysis Method | % Yield[b] |
|---|---|---|---|---|---|
| Triisopropyl | | | | | |
| 0.1 | 0.8 | 0.12 (p) | 100 | base | 85 |
| 0.12 | 0.8 | 0.1 (p) | 100 | base | 77 |
| 0.1 | 0.8 | 0.12 | 100 | base | 70 |
| 0.1 | 0.2 | 0.12 (p) | 100 | acid | 79 |
| Tri-n-butyl | | | | | |
| 0.1 | 0.8 | 0.12 (p) | 100 | base | 73[c] |
| 0.1 | 0.5 | 0.1 (p) | 100 | base | 32[c] |
| 0.1 | 0.8 | 0.2 | 100 | base | 63[c] |
| 0.1 | 0.8 | 0.12 | 100 | base | 85 |
| Trimethyl | | | | | |
| 0.1 | 0.8 | 0.12 (p) | 60 | acid | 74 |
| Tri-sec-butyl | | | | | |
| 0.05 | 0.41 | 0.12 (p) | 120 | base | 75 |

[a]Formaldehyde was charged as a 37% solution in water. (p) denotes when paraformaldehyde was used.
[b]Yields determined by $^{31}$P-NMR and are based on moles of phosphite charged.
[c]Reactions were run for 6 hours.

Example 3

This comparative example illustrates the use of various dialkylphosphites in the synthesis of N-(2-hydroxyethyl) aminomethylphosphonic acid.

Diisopropylphosphite (17 g, 0.1 mmol), paraformaldehyde (3.6 g, 0.12 mmol) and ethanolamine (48.8 g, 0.8 mmol) was charged into a round bottom flask equipped with magnetic stir bar and reflux condenser. The reaction was heated to 100° C. for 16 h. Base hydrolysis of the intermediate esters was achieved by adding 2 equiv. of NaOH (16 g of a 50% solution) and heating to 120° C. for 16 hours. The reaction was allowed to cool and was concentrated under vacuum. Water (30 mL) was added to the reaction mixture and a sample was removed for $^{31}$P-NMR analysis. Yield of N-(2-hydroxyethyl)aminomethylphosphonic acid (13%) was based on moles of phosphite charged.

Summarized in Table 3 are the results of reactions run with a similar experimental protocol as described above but with different dialkylphosphites and various ratios of reagents.

TABLE 3

Preparation of N-2-Hydroxyethylaminomethylphosphonic Acid Using a Variety of Dialkylphosphites

| Phosphite | Mole Ethanolamine | Formaldehyde[a] | Reaction Temp °C. | Hydrolysis Method | % Yield[b] |
|---|---|---|---|---|---|
| Dimethyl 0.1 | 0.8 | 0.12 (p) | 80 | base | 20 |
| Diethyl 0.1 | 0.8 | 0.1 (p) | 70 | acid | 18[c] |
| Diisopropyl 0.1 | 0.8 | 0.12 (p) | 100 | base | 13 |
| Di-sec-butyl 0.1 | 0.8 | 0.12 (p) | 100 | base | 15 |

[a]Formaldehyde was charged as a 37% solution in water. (p) denotes when paraformaldehyde was used.
[b]Yields determined by $^{31}$P-NMR and are based on moles of phosphite charged.
[c]Reactions were run for 6 hours.

Comparing the results in Tables 1 and 2 with the results in Table 3 clearly demonstrate the unexpected improvement in yields achievable with trialkylphosphites in the process of the invention.

Example 4

This example illustrates the preparation of N-(2-hydroxylethyl)aminomethylphosphonic acid by hydrolysis of the intermediate phosphonate esters with NaOH using an alcohol as the solvent.

A solution of paraformaldehyde (4 g, 0.13 mol), ethanolamine (48.8 g, 0.8 mmol) and triisopropylphosphite (20.8 g, 0.1 mmol) was stirred at 100° C. for 16 hours. The reaction was allowed to cool to room temperature and 8 ml of 50% w/w sodium hydroxide and 100 ml of isopropanol were added. The mixture was heated to reflux for 48 h. The solution was concentrated under vacuum and 25 ml of distilled water was added to homogenize the mixture. The reaction was analyzed by $^{31}$P-NMR in D$_2$O at pH=0.7. N-(2-Hydroxylethyl)aminomethylphosphonic acid was obtained in 80% yield.

Example 5

This is a comparative example which illustrates the procedure reported by Barsukov et al, "Synthesis of New Complexons and Their Derivatives", Zhurnal Obshchei Khimii, Vol. 53, No. 6, pp 12243–49 (1983) for the preparation of N-(2-hydroxyethyl)aminomethylphosphonic acid utilizing dimethylphosphite.

Dimethylphosphite (36 g, 0.3227 mole) was added dropwise over a period of 1 hour to a stirring solution of paraformaldehyde (9.8 g, 0.32 mole) and ethanolamine (20 g, 0.32 mole) below 20° C. under nitrogen. The solution was heated to 80° C. for 1 hour and then cooled to room temperature. The solution was extracted with 350 ml of benzene as described in the paper. The benzene solution was then passed through a column containing 1 kg of alumina and the column was eluted with 1 liter of benzene. The benzene solution was concentrated under vacuum to dryness and 250 mL of Conc. HCl was added. The solution was heated to 110° C. for 6 hours. Analysis of the reaction mixture by $^{31}$P-NMR showed 0% yield of N-(2-hydroxyethyl)aminomethylphosphonic acid. This Example demonstrates that contrary to what is disclosed in the Barsukov et al reference, the process taught in the Barsukov et al reference produces no N-(2-hydroxyethyl)aminomethylphosphonic acid.

Example 6

This example illustrates the use of an alcohol solvent in the production of N-(2-hydroxyethyl)aminomethylphosphonic acid using a trialkylphosphite.

A solution of paraformaldehyde (4.0 g, 0.122 mole), ethanolamine (12 g, 0.2 mole), triisopropylphosphite (20.9 g, 0.1 mole) and 50 mL of isopropanol was stirred at 90° C. for 16 hours. The isopropanol was removed under vacuum and 50 mL of conc. HCl was added in one portion. The solution was heated at reflux for 6 hours after which time it was assayed by $^{31}$P-NMR. N-(2-Hydroxyethyl)aminomethylphosphonic acid was obtained in 78% yield.

Example 7

This example illustrates the use of the Raney copper catalyst containing chromium of U.S. Pat. No. 5,292,936 to convert N-(2-hydroxyethyl)aminomethylphosphonic acid to N-phosphonomethylglycine.

Into a 160 ml nickel autoclave equipped with a stirrer is charged N-2-(hydroxyethyl)aminomethylphosphonic acid (16.84 g, 0.11 mol.) water (11.3 ml) and 45 weight % potassium hydroxide (48.7 g, 0.39 mol.) and Raney copper catalyst containing 943 parts per million chromium (3.53 g). The autoclave is sealed and heated to 160° C. under a pressure of 9.5 Kg/cm$^2$ while stirring the liquid phase in the autoclave. After 1.85 hours, hydrogen evolution ceases. The yield of N-phosphonomethylglycine as its potassium salt is 98.5%.

Example 8

This example illustrates the preparation of the supported mixed metal catalyst of the present invention.

Into a one-liter glass beaker containing a teflon coated, 5 centimeter long, magnetic stirring bar, on a magnetic stirring plate are added distilled water (169 ml) and wet 5% platinum on activated carbon in powder form, available from Degussa Corporation of Ridgefield Park, N.J., which corresponds to 13.37 grams on a dry weight basis. In a separate one-liter beaker a copper plating solution is prepared by adding the following components, most of which are available from MacDermid, Inc. of Waterbury, Conn., with stirring in the following order:

(1) 687 ml deionized water
(2) 90 ml MACuPlex Ultra Dep 1000B,
(3) 54 ml MACuPlex Ultra Dep 1000A,
(4) 18 ml MACuPlex Ultra Dep 1000D,
(5) 5 ml 37% w/w formaldehyde * proprietary products of MacDermid TOTAL VOLUME 854 ml According to MacDermid's product description for Product Code No. 17970, the resulting aqueous solution comprises the following active ingredients:

Copper sulfate 4.0 g/l
Formaldehyde 6.0 g/l
Sodium hydroxide 9.0 g/l
Excess EDTA chelant 0.06 molar The resulting plating solution is filtered and then added to the slurry of the 5% platinum on activated carbon by adding 122 milliliter increments every 3 minutes at 40° C. The pH is monitored to verify the extent of the reaction. Time between additions is extended when gas evolution becomes too vigorous.

After the addition of the plating solution is completed, the catalyst is recovered by filtration using a 4 liter vacuum flask, a 350 ml coarse glass filter funnel, and a glass dome over the top of the funnel with nitrogen. After filtration, the solid material is washed with three to four 250 milliliter portions of deionized water. The dry weight yield in this preparation is 18.4 grams. Microanalysis of the catalyst shows the elemental composition to be 13.4 wt. % copper and 3.4 wt. % platinum, based on the total weight of the catalyst. The average copper crystal size as determined by XRD line broadening is found to be 157 Angstroms.

Example 9

This example shows another preparation of the supported mixed metal catalyst of the present invention.

To a 2-liter glass beaker containing a Teflon polymer coated, 2.5 centimeter long, magnetic stirring bar on a magnetic stir plate is added distilled water (190 ml) followed by 5 wt. % platinum on activated carbon, available from Degassa Corporation, corresponding to 16.42 grams (dry weight). An aqueous copper plating solution is prepared in a 4 liter beaker by adding the following components with stirring.

(1) 500 ml DI water (2) $NaKC_4H_4O_6 \cdot 4 H_2O$ (tartrate) [29.99 g, 0.106 moles]; stir to dissolve (3) In a separate beaker, dissolve 11.79 gms of $CUSO_4 \cdot 5 H_2O$ (3 gms Cu), (0.047 moles) in 400 ml deionized water (4) Add copper solution (3) to the resulting tartrate solution (2)

(5) Add 13.60 grams of 50 wt % NaOH [0.17 mole]

(6) 11.35 ml 37 wt. % formaldehyde [0.15 mole]

TOTAL VOLUME 1125 ml

The resulting plating solution is added to the slurry of 5 wt. % platinum on carbon in a total of about twelve, 79 ml increments with one increment every 2.5 minutes. The pH is monitored to verify the extent of the reaction and to delay incremental addition in time if and when the solution degassing becomes too vigorous. The catalyst, after the plating solution is added to the slurry, is recovered by filtration as in Example 9. The dry weight yield is 20.03 grams. The composition is analyzed and is found to be 14.5% copper and 3.8% platinum, based on the total weight of the catalyst. The average copper crystal dimension is 119 Angstroms.

Example 10

This example illustrates the use of various trialkylphosphites in the synthesis of N-(2-hydroxyethyl) aminomethylphosphonic acid using a low molar ratio of ethanolamine to phosphite and removing alcohol during the hydrolysis by distillation, and the unexpectedly high yield and selectivity when trialkylphosphites with alkyl groups having 3–4 carbon atoms, particularly triisopropylphosphite, are used.

A solution of 37% aqueous formaldehyde (8.2 g, 0.1 mole) and ethanolamine (9.0 g, 0.15 mole) was stirred at room temperature for 1 hour followed by the addition of triisopropylphosphite (22 g, 0.1 mole). The reaction solution was heated at 80° C. for 3 hours. Water (50 mL) and 16 mL of 50% NaOH was added to the reaction and the mixture was distilled in a Dean-Stark apparatus for 3 hours at 150° C. to hydrolyze the intermediate esters with the simultaneous removal of water, isopropanol and ethanolamine. A white precipitate formed which was dissolved with an additional 50 mL of water. Analysis of the reaction mixture by $^{31}P$-NMR showed a 98% yield of N-(2-hydroxyethyl) aminomethylphosphonic acid and 2% yield of bis-N-(2-hydroxyethyl)aminomethylphosphonic acid.

Summarized in Table 4 are the results of reactions run with a similar experimental protocol as described above but with different trialkylphosphites.

TABLE 4

Preparation of N-Hydroxyethylaminomethylphosphonic Acid Using a Variety of Trialkyphosphites

| Phosphite | Mole Ethanolamine | Formaldehyde | Temp °C. | % Yield Mono[a] | Bis[b] |
|---|---|---|---|---|---|
| Trimethyl | | | | | |
| 0.1 | 0.15 | 0.10 | 80 | 26 | 23 |
| Triethyl | | | | | |
| 0.1 | 0.15 | 0.10 | 80 | 55 | 4 |
| Triisopropyl | | | | | |
| 0.1 | 0.15 | 0.10 | 80 | 98 | 2 |
| Tributyl | | | | | |
| 0.1 | 0.13 | 0.10 | 80 | 84 | 4 |
| Trihexyl | | | | | |
| 0.1 | 0.15 | 0.10 | 80 | 55 | 3 |

[a]N-(2-hydroxyethyl)aminomethylphosphonic acid.
[b]bis-N-(2-hydroxyethyl)aminomethylphosphonic acid.

Example 11

This example illustrates the production of N-(2-hydroxyethyl)aminomethylphosphonic acid when 1.2 equivalents of ethanolamine are used in the reaction.

A solution of 37% aqueous formaldehyde (8.2 g, 0.1 mole) and ethanolamine (7.2 g, 0.12 mole) was stirred at room temperature for 2 hours followed by the addition of triisopropylphosphite (22 g, 0.1 mole). The reaction solution was heated at 80° C. for 3 hours. Water (50 mL) and 17 mL of 50% NaOH was added to the reaction and the mixture was distilled in a Dean-Stark apparatus for 3 hours at 150° C. to hydrolyze the intermediate esters with the simultaneous removal of water, isopropanol and ethanolamine (~70 mL total). A white precipitate formed which was dissolved with an additional 50 mL of water. Analysis of the reaction mixture by $^{31}P$-NMR showed a 90% yield of N-(2-hydroxyethyl)aminomethylphosphonic acid and 4% yield of bis-N-(2-hydroxyethyl)aminomethylphosphonic acid.

Example 12

This comparative example illustrates the production of N-(2-hydroxyethyl)aminomethylphosphonic acid using diisopropylphosphite.

A solution of 37% aqueous formaldehyde (8.2 g, 0.1 mole) and ethanolamine (9 g, 0.15 mole) was stirred at room temperature between one and two hours followed by the addition of diisopropylphosphite (17 g, 0.1 mole). The reaction solution was heated at 80° C. for 3 hours. Water (50 mL) and 16 mL of 50% NaOH was added to the reaction and the mixture was distilled in a Dean-Stark apparatus for 3 hours at 150° C. to hydrolyze the intermediate esters with the simultaneous removal of water, isopropanol and ethanolamine (80–100 mL total volume removed). A white precipitate formed which was dissolved with an additional 50 mL of water. Analysis of the reaction mixture by $^{31}$P-NMR showed a 49% yield of n-(2-hydroxyethyl) aminomethylphosphonic acid and 6% yield of bis-N-(2-hydroxyethyl)aminomethylphosphonic acid.

Comparing the results in this example with the results with triisopropyl phosphite in Example 10 clearly demonstrate the unexpected improvement in yield achievable with trialkylphosphite in the process of the invention.

Example 13

This example illustrates the water hydrolysis of intermediate esters of N-hydroxyethylaminomethylphosphonic acid.

A reaction was conducted under conditions identical to those described in Example 11 using triisopropyl phosphite except that after the three hour reaction time the reaction mixture was concentrated under vacuum to give a yellow oil. A portion of the oil (4.2 g) was transferred to a steel bomb reactor and 20 mL of distilled water was added. The reactor was sealed and was heated to 220° C. for 10 hours. Analysis of the reaction by $^{31}$P-NMR showed partial hydrolysis (50%) to N-hydroxyethylaminomethylphosphonic acid.

That which is claimed is:

1. A process for preparing N-hydroxyalkylaminomethylphosphonic acid represented by the formula

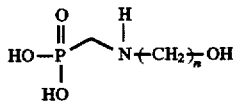

or salts thereof comprising:

(a) contacting an alkanolamine represented by the formula

wherein n is 2 to 6, formaldehyde and a trialkyl phosphite under suitable conditions of time and temperature to produce a reaction mixture wherein the molar ratio of alkanolamine to phosphite is about 1:1 to about 15:1, and (b) hydrolyzing said reaction mixture under neutral, acidic or basic conditions.

2. The process of claim 1 wherein said reaction of (a) is conducted in the presence of an alcohol.

3. The process of claim 1 wherein the molar ratio of formaldehyde to phosphite is 1:1 to about 5:1.

4. The process of claim 3 wherein the alkyl groups of said trialkyl phosphite have 3 to 4 carbon atoms.

5. The process of claim 1 wherein said trialkyl phosphite is triisopropyl phosphite.

6. The process of claim 1 wherein the molar ratio of alkanolamine to phosphite is about 1.2:1 to about 8:1 and the number of carbon atoms in the alkyl group of said trialkyl phosphite is 2 to 6.

7. The process of claim 6 wherein said trialkyl phosphite is triisopropyl phosphite.

8. The process of claim 1 wherein the molar ratio of alkanolamine to phosphite is about 1:1 to about 10:1 and the number of carbon atoms in the alkyl group of said trialkyl phosphite is 1 or greater than 6.

9. The process of claim 1 wherein the hydrolysis is conducted under basic conditions.

10. The process of claim 9 wherein said hydrolysis is conducted in the presence of an alkali metal hydroxide or alkaline earth metal hydroxide.

11. The process of claim 9 wherein alcohol formed during said hydrolysis is removed during said hydrolysis.

12. The process of claim 1 wherein n is 2.

13. The process of claim 1 further comprising:

(c) catalytically oxidizing said N-hydroxyalkylaminomethylphosphonic acid or salts thereof to produce an N-phosphonomethylaminocarboxylic acid represented by the formula

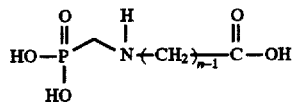

or salts thereof.

14. The process of claim 12 wherein the oxidation is conducted by contacting said N-hydroxyalkylaminomethylphosphonic acid or salts thereof with an alkali metal hydroxide in the presence of an effective amount of a Raney copper catalyst containing from about 50 to about 10,000 parts per million of an element selected from the group consisting of chromium, titanium, niobium, tantalum, zirconium, vanadium, molybdenum, manganese, tungsten, cobalt, nickel and mixtures thereof.

15. The process of claim 13 wherein the oxidation is conducted in the presence of an effective amount of a carbon supported mixed metal catalyst.

16. The process of claim 15 wherein said catalyst is a carbon supported mixture of Cu and Pt or Pd.

17. The process of claim 1 wherein said temperature of the reaction of (a) is about 50° C. to about 150° C.

18. A process for preparing N-phosphonomethylglycine or salts thereof comprising:

(a) contacting ethanolamine, formaldehyde and a trialkyl phosphite under suitable reaction conditions of time and temperature to produce a reaction mixture wherein the molar ratio of ethanolamine to phosphite is about 1:1 to about 15:1, (b) hydrolyzing said reaction mixture under neutral, acidic or basic conditions to produce N-hydroxyethylaminomethylphosphonic acid or salts thereof, and (c) catalytically oxidizing said N-hydroxyethylaminomethylphosphonic acid or salts thereof.

19. The process of claim 18 wherein said trialkyl phosphite is triisopropyl phosphite.

20. The process of claim 18 wherein the oxidation is conducted by contacting said N-hydroxyalkylaminomethylphosphonic acid or salts thereof with an alkali metal hydroxide in the presence of an effective amount of a Raney copper catalyst containing from about 50 to about 10,000 parts per million of an element selected from the group consisting of chromium, titanium, niobium, tantalum, zirconium, vanadium, molybdenum, manganese, tungsten, cobalt, nickel and mixtures thereof.

21. The process of claim 18 wherein the oxidation is conducted in the presence of an effective amount of a carbon supported mixed metal catalyst.

22. The process of claim 18 wherein the hydrolysis is conducted under basic conditions.

23. The process of claim 22 wherein the hydrolysis is conducted in the presence of an alkali metal hydroxide or alkaline earth metal hydroxide.

24. The process of claim 22 wherein alcohol formed during said hydrolysis is removed during said hydrolysis.

25. The process of claim 18 wherein said reaction of (a) is conducted in the presence of an alcohol.

26. The process of claim 18 wherein the molar ratio of ethanolamine to phosphite is about 1.2:1 to about 8:1 and the number of carbon atoms is the alkyl group of said trialkyl phosphite is 2 to 6.

27. The process of claim 26 wherein said trialkyl phosphite is triisopropyl phosphite.

28. The process of claim 18 wherein the molar ratio of alkanolamine to phosphite is about 1:1 to about 10:1 and the number of carbon atoms in the alkyl group of said trialkyl phosphite is 1 or greater than 6.

29. The process of claim 18 wherein the molar ratio of formaldehyde to phosphite is 1:1 to about 5:1.

30. A process for preparing N-hydroxyalkylaminomethylphosphonic acid represented by the formula

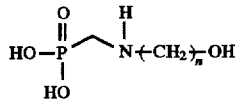

or salts thereof comprising:
(a) contacting an alkanolamine represented by the formula $H_2N\text{-}(CH_2)_n\text{-}OH$ wherein n is 2 to 6, formaldehyde and a trialkyl phosphite in the presence of an alcohol represented by the formula $R(OH)_m$ wherein R is an alkyl group having 1 to about 18 carbon atoms and m is 1 to 3, under suitable conditions of time and temperature to produce a reaction mixture wherein the molar ratio of alkanolamine to phosphite is about 1:1 to about 5:1, and
(b) hydrolyzing the reaction mixture under neutral, acidic or basic conditions.

31. The process of claim 30 wherein said trialkyl phosphite is triisopropyl phosphite.

32. The process of claim 30 wherein n is 2.

33. The process of claim 30 wherein the molar ratio of alkanolamine to phosphite is 1:1 to about 2:1.

34. The process of claim 30 further comprising:
(c) catalytically oxidizing said N-hydroxyalkylaminomethylphosphonic acid or salts thereof to produce an N-phosphonomethylaminocarboxylic acid represented by the formula

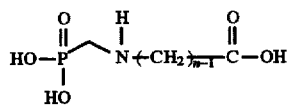

or salts thereof.

35. The process of claim 34 wherein the oxidation is conducted by contacting said N-hydroxyalkylaminomethylphosphonic acid or salts thereof with an alkali metal hydroxide in the presence of an effective amount of a Raney copper catalyst containing from about 50 to about 10,000 parts per million of an element selected from the group consisting of chromium, titanium, niobium, tantalum, zirconium, vanadium, molybdenum, manganese, tungsten, cobalt, nickel and mixtures thereof.

36. The process of claim 34 wherein the oxidation is conducted in the presence of an effective amount of a carbon supported mixed metal catalyst.

37. The process of claim 30 wherein the hydrolysis is conducted under basic conditions.

38. The process of claim 37 wherein alcohol formed during said hydrolysis is removed during said hydrolysis.

39. The process of claim 4 wherein the molar ratio of alkanolamine to phosphite is about 1.5:1 to about 2.5:1.

40. The process of claim 39 wherein said trialkyl phosphite is triisopropyl phosphite.

41. The process of claim 39 where in the molar ratio of formaldehyde to phosphite is 1:1 to about 2:1.

* * * * *

UNITED STATES PATENT AND TRADEMARK OFFICE
CERTIFICATE OF CORRECTION

PATENT NO.    :   5,703,273

DATED         :   December 30, 1997

INVENTOR(S)   :   Michael K. Stern et al.

It is certified that error appears in the above-identified patent and that said Letters Patent is hereby corrected as shown below:

On the title page, in the section labeled "U.S. PATENT DOCUMENTS," please delete "4,062,491" and insert therefor -- 4,065,491 --.

In claim 14, column 16, line 24, please delete "12" and insert therefor --13--.

Signed and Sealed this

Seventh Day of April, 1998

Attest:

BRUCE LEHMAN

*Attesting Officer*    *Commissioner of Patents and Trademarks*